United States Patent [19]
Roy

[11] Patent Number: 4,601,465
[45] Date of Patent: Jul. 22, 1986

[54] DEVICE FOR STIMULATING THE HUMAN RESPIRATORY SYSTEM

[76] Inventor: Jean-Yves Roy, 5091, 18e Avenue, Montreal, Quebec, Canada, H1X 2N8

[21] Appl. No.: 592,474

[22] Filed: Mar. 22, 1984

[51] Int. Cl.[4] .................. A63B 23/00; A61M 16/00
[52] U.S. Cl. ......................... 272/99; 128/207.16; 128/720; 128/725
[58] Field of Search .............. 272/99; 128/207.16, 128/720, 725

[56] References Cited

U.S. PATENT DOCUMENTS

| | | | |
|---|---|---|---|
| 957,548 | 5/1910 | Doane | 272/99 |
| 3,946,726 | 3/1976 | Pikul | 128/725 |
| 4,054,134 | 10/1977 | Kritzer | 128/207.16 X |
| 4,060,074 | 11/1977 | Russo | 272/99 X |
| 4,086,918 | 5/1978 | Russo | 272/99 X |

OTHER PUBLICATIONS

Soviet Review of Sports, 9/1982, pp. 154–155, *A Mouthpiece for Endurance Training*, V. V. Kim.

Primary Examiner—Robert A. Hafer
Assistant Examiner—Kathleen D'Arrigo
Attorney, Agent, or Firm—Robic, Robic and Associates

[57] ABSTRACT

A device for stimulating the human respiratory system by making breathing more difficult and limiting lung ventilation. The device comprises a mouth-piece for insertion in the mouth of a person, or a mask attachable to the face of this person. The mouth-piece or mask has a central opening through which the person may breathe. A tubular body defining an air duct is connected at one end to the mouth-piece or to the mask with the air duct in alignment and communication with the opening. The device also comprises a membrane mounted in the tubular body at the other end thereof to put up a breathing resistance in at least one respiratory direction. Proper stimulation is obtained when use is made of a tubular body long enough to increase the dead space of the respiratory system of the person using the device.

5 Claims, 7 Drawing Figures

DEVICE FOR STIMULATING THE HUMAN RESPIRATORY SYSTEM

BACKGROUND OF THE INVENTION (a) field of the invention

The present invention relates to a device for stimulating the human respiratory system by mere increase of the respiratory organs activity (b) brief description of the prior art It is well known that regular stimulation of the thoracic musculature is of a great interest for those who wish to develop their aerobic endurance, to increase their respiratory organs functional capabilities and to improve their lung ventilation. These development, increase and/or improvement can be particularly useful for the athletes who wants to develop their endurance in some athletic activities, or the paraplegics or other disabled who want to exercise their abdominal muscles to recover, for example, from a surgical operation.

The object of the present invention is to provide a device for stimulating the human respiratory system by making breathing more difficult and limiting lung ventilation, which device is simple in structure, small in size and little expansive.

By way of examples, the device according to the invention can be used for stimulating the inspiratory and expiratory muscles, for stimulating the osseous and cartilagineous structures of the thorax, especially in youths, and for increasing the aerobic working capacity.

Up to now, this kind of stimulation and development has been obtained by practising physical activities of the aerobic type, by using an altitude simulator, or in hospitals, by blowing air at the bottom of a vertical tube containing a column of water.

The main problem with the practice of physical activities of the aerobic type is that the respiratory muscles are rarely and never specifically exercised to a sufficient extent. Indeed, the other muscles and the articulations are overworked and become sources of pains in most of the cases well before the respiratory muscles, thereby preventing adequate training of the cardiovascular system. An altitude simulator permits to exercise the respiratory muscles in a way similar to the instant invention. However, such a simulator is very expansive and very voluminous (20 to 25 times bigger and at least 50 times heavier than the device according to the invention). Last of all, the apparatuses used in hospitals to stimulate the respiratory activity are efficient but not very easy to transport and therefore use under normal conditions.

SUMMARY OF THE INVENTION

The device according to the invention is particularly designed and well adapted for practising physical activities, such as jogging, athletic exercises and the like. This device is very compact in size and not heavy, thereby making it easy to be carried in the mouth or over the face of the person using it.

The device according to the invention for stimulating the human respiratory system by making breathing more difficult and limiting lung ventilation basically comprises:

a mouth-piece for insertion in the mouth of the person, or alternatively a mask attachable to the face of this person, this mouth-piece or mask having a central opening through which the person may breathe;

a tubular body defining an air duct, this body being connected at one end to the mouth-piece or to the mask, with the air duct in alignment and communication to the opening; and obstruction means preferably removable and reversible, mounted within a tubular body at the other end thereof to put up a breathing resistance in at least one respiratory direction.

When use is made of a mouth-piece, the tubular body, the mouth-piece and the obstruction means are designed to be very compact in size and light enough to be carried exclusively through the mouth-piece when the same is inserted in the person's mouth.

When use is made of a mask, the tubular body, the obstruction means and the mask are designed to be light enough to be carried exclusively through the mask when the same is attached onto the person's face.

In both cases, the length of the tubular body is advantageously selected to increase the dead space of the respiratory system of the person using the device, so as to improve the stimulation already obtained due to the obstruction means which put up a breathing resistance in at least one and, if desired, both respiratory directions.

According to a preferred embodiment of the invention, the air-duct at the end of the tubular body which is opposite to the mouth-piece or to the mask, is divided into two separate passages. In this particular case, the obstruction means are mounted in only one of the passages while a check-valve is mounted in the other passage to allow air to be freely breathed in at least one of the respiratory directions.

If desired, the obstruction means may be designed to provide a breathing resistance in both the inspiratory and expiratory directions while the check-valve comprises means to make it detachable and reversible, thereby permitting selection of the direction in which air is allowed to be freely breathed in the passage in which the check valve is mounted.

The obstruction means may consist of a membrane permeable to air. This permeable membrane may be a piece of fabric made of natural or synthetic textile fibers loosely woven to allow passage of air, or a rigid membrane provided with a plurality of small perforations wide enough to allow air to pass therethrough. The obstruction means may also consist of an impermeable membrane made of rubber or plastic and provided with a central hole having a diameter smaller than the diameter of passage in which it is mounted.

The person using the device may have several membranes each capable of putting up a different resistance to air due to a variation in the number of holes, or the diameter thereof. Each membrane is advantageously mounted in a removable manner, to allow replacement of a membrane by another. Advantageously, the two passages of the tubular body are parallel and adjacent.

According to another preferred embodiment of the invention, the tubular body is not divided into two separate passages. In this case, the obstruction means at the end of the tubular body advantageously comprises:

a rigid membrane permeable to air, this membrane extending transversally across a portion of the air duct and providing a rigid edge transversal to this air duct; and a flexible membrane transversely mounted across the air duct, this membrane covering the portion of the air duct not covered by the rigid membrane and overlapping at least part of the rigid membrane close to its rigid edge to form with this rigid membrane a check valve.

This particular combination of rigid and flexible membranes allows air to be freely breathed as it would be through a check valve in one respiratory direction, while it is subject to a breathing resistance through the rigid membrane permeable to air in the other direction.

In this particular embodiment, the flexible membrane is preferably also permeable to air. As permeable membranes, use can be made of pieces of rubber or plastic provided with a plurality of small perforations.

Preferably, the rigid and flexible membranes are both mounted onto a same ring detachably mounted in a reversible manner in the tubular body, to make them replaceable by another set of membranes of different air resistance mounted onto another ring. Such a mounting also permits to reverse the ring to make the check valve operating in the other direction.

The device for stimulating the human respiratory system according to the invention is particularly interesting in that it permits to stimulate the inspiratory muscles, the expiratory muscles or both of them simultaneously, according to the user's requirements. It also permits to adapt the training by using membranes of different resistance making breathing more or less difficult.

The device according to the invention is therefore particularly interesting for developing endurance and for increasing the respiratory capabilities, including maximum ventilatory capacity; inspiratory force; expiratory force, vital capacity and maximum aerobic capacity. Increase of the maximum aerobic capacity can particularly be obtained by stimulating the respiratory muscles while the other muscles are simultaneously stimulated by a training or any other kind of athletic activities.

The device according to the invention can therefore be used for developing endurance and strength of the respiratory muscles, thereby increasing the body's adaptive capacity and the organ's functional capability and leading to more efficient oxygen utilisation. This makes the device according to the invention useful in any kind of training activities, including jogging, cross-country skiing, swimming and cycling.

As indicated hereinabove, use can be made of a mouth-piece constructed of flexible material such as rubber. Use may alternatively be made of a mask covering both the nose and mouth of the trainer, thereby forcing him or her to breath exclusively through the device.

BRIEF DESCRIPTION OF THE DRAWINGS

The invention and its numerous advantages will be better understood in light of the following non-restrictive description made with reference to the accompanying drawings wherein.

DESCRIPTION OF SEVERAL PREFERRED EMBODIMENTS

Figure 1:
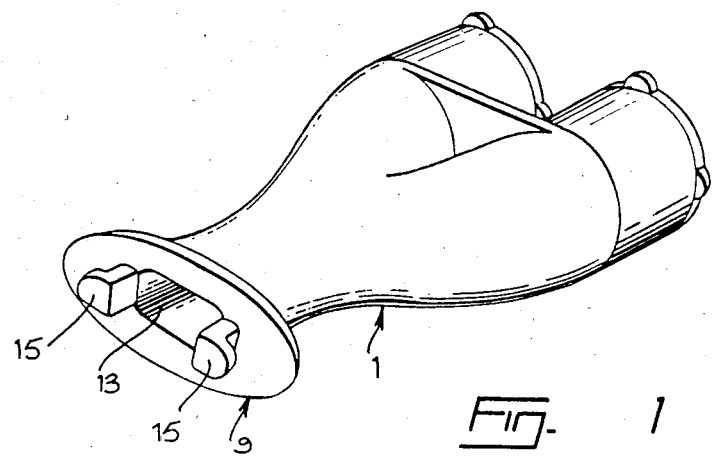
FIG. 1 is a perspective view of a first embodiment of the stimulating device according to the invention.

The device for stimulating the human respiratory system as shown in FIGS. 1 to 4 comprises a hollow body 1 defining an air duct 3 (see FIG. 3) which is divided at one end into two parallel passages 5 and 7.

The body 1 is provided at one end with a mouthpiece 9 capable being inserted in the mouth of the user of the device. This mouth-piece comprises a thin, slightly curved element 11 made of semi-flexible material, which element is intended to be inserted between the lips and the gums and teeth of the user. The element 11 comprises a central opening 13 which is in alignment and direct communication with the inlet opening of the air duct 3. Two L-shaped projection are provided on both side of the opening 13, for insertion between the teeth of the user. These projections advantageously cooperate with the element 11 to keep the device according to the invention rigidly in position in the mouth of the user.

Obstruction means are mounted in a removable manner transversely across the end of the passage 5. As better shown in FIG. 2, the obstructions means may consist of a disc 17 made of rigid material such as rigid rubber, rigid plastic or any other non-oxydizable material. The disc 17 is provided with a predetermined number of holes 19 to make it permeable to air. The periphery of the disc 17 bears against a shoulder 21 provided inside the passage 5 and is held in position by means of a ring 22 provided with an external thread making it screwable inside the end of the passage 5 which is opposite to the mouth piece 9. This opposite end of course comprises a corresponding thread. The ring 22 comprises a flange 23 at its end which is opposite to the shoulder 21, which flange acts as a stop with respect to the end of the passage 5. A plurality of fingers 25 may be provided all around the flange 23 to facilitate hand-grasping and insertion of the ring 22 in the passage 5.

Figures 4, 6:
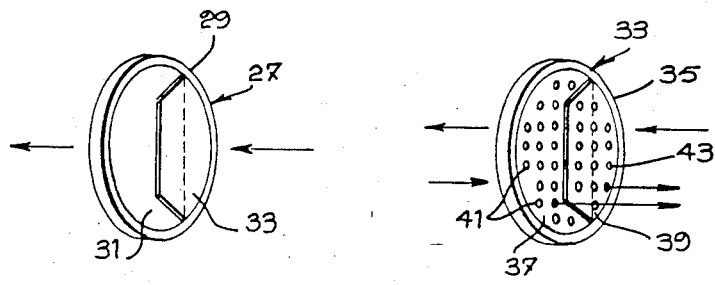
FIG. 4 appearing on the same sheet of drawing as FIG. 1, is an enlarged view of the check valve mounted in one of the passages of the device shown in FIGS. 1, 2 and 3.
FIG. 6 is a perspective view of the obstruction membrane used in the device of FIG. 5.
Figure 3:
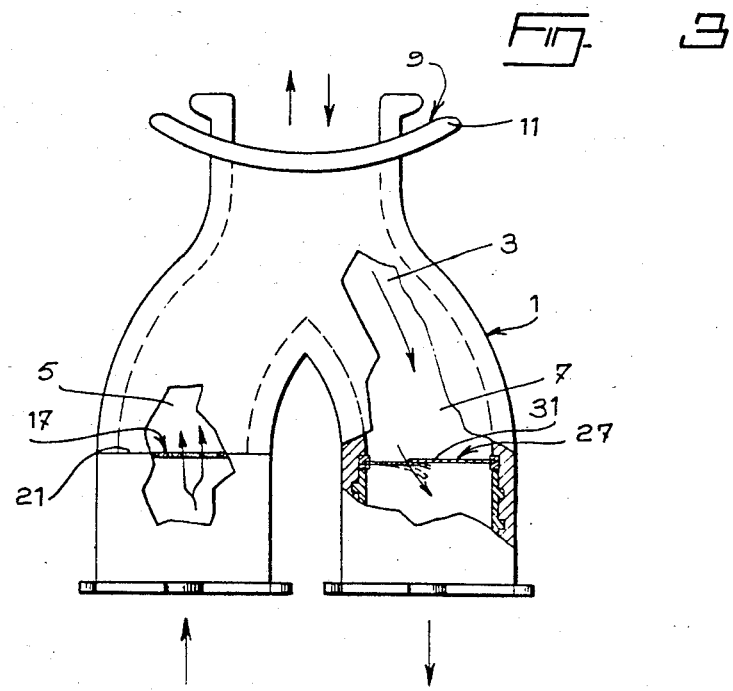
FIG. 3 is a top plan view of the device shown in FIGS. 1 and 2, with part of its wall removed to show its internal structure and some of its elements.

The other passage 7 is provided with a check valve 27 shown in greater detail in FIGS. 3 and 4. This check valve 27 comprises a ring 29 supporting a rigid membrane 31 extending over a portion of the central hole defined by the ring 29. A flexible membrane 33 is also fixed to the ring 29, more particularly onto the side of the ring which is opposite to the side onto which the rigid membrane 31 is fixed. The dimension and shape of the membranes 31 and 33, as clearly shown in FIGS. 3 and 4, are determined in such a manner that the membrane 33 slightly overlaps the membrane 31 and normally bears against this membrane 31 when the membrane 33 is not subject to any air pressure.

The check valve 27, as shown in FIG. 3, is mounted inside the passage 7 exactly in the same manner as the disc 17 in the passage 5. For this reason, the way the check valve 27 may be mounted will not be further described. It must however be kept in mind is that the check valve 27 is mounted inside the passage 7 in a removable and reversible manner.

As can now be easily understood, the device according to the invention works as follows when use is made of the particular arrangement shown in FIG. 3: during inspiration, air enters the passage 5 in the way indicated by means of arrows. The perforated disc 17 of course puts up a resistance to the passage of air, which resistance varies according to the number, position and diameter of the holes 19. During expiration, air will <select> the easiest way. Accordingly, air will go through the passage 7 where is located the check valve 27, this check-valve letting air escape by mere flexion of its membrane 33.

As can be also understood, mere reversal of the check valve 27 inside the passage 7 will cause air to enter easily the passage 7 during inspiration while it will be forced to escape through the passage 5 and therefore through the disc 17 during expiration.

As a result, the device for stimulating the respiratory system as shown in FIGS. 1 to 4 permits to stimulate either the inspiratory or expiratory muscles, be mere selection of the direction of operation of the checkvalve 27.

Of course, if an obstruction disc similar to the one used in passage 5 is also inserted in passage 7, it may become possible to exercise and stimulate both the inspiratory and expiratory muscles.

As previously mentioned, the disc 17 may be replaced by a piece of fabric made of loosely woven fibers capable of allowing air to pass. This piece of fabric must of course be sufficiently thick and rigid to perform its function.

Figure 5:
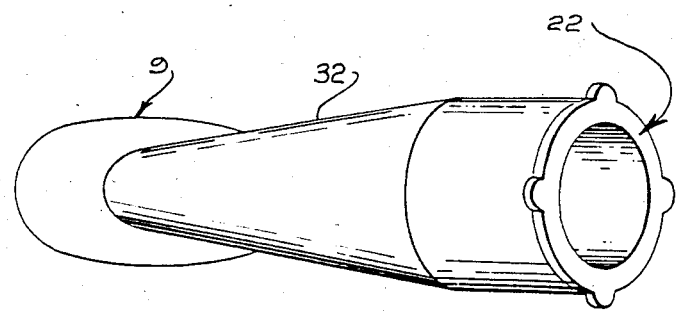
FIG. 5 appearing on the same sheet of drawing as FIG. 1, is a perspective view of another embodiment of the invention.

The device for stimulating the human respiratory system as shown in FIG. 5, is of the same type as the one shown in FIGS. 1 to 4, except that it comprises a single, non-divided air duct 32 provided at one end with a mouth piece 9 and at the other end with a ring 22 similar to the one described hereinabove. The ring 22 is mounted in the same manner as previously described.

In this particular embodiment, use is however made of obstruction means 33 capable of controlling circulation of air in both directions. These means 33 comprise a ring 35 supporting a rigid membrane 37 which is permeable to air. Although the membrane 37 allows air to pass therethrough, it creates a substantial breathing resistance. The membrane 37 extends over a portion only of the central hole defined by the ring 35. A flexible membrane 39 is connected to the ring 35 on the side of this ring which is opposite to the side on which the membrane 37 is fixed, to cover the remaining portion of the central hole not covered by the rigid membrane 37. The flexible membrane 39 is sized to overlap the rigid membrane 37 close to its edge to form with this rigid membrane a check valve allowing air to pass with given resistance in one way through the rigid, permeable membrane 37, and to pass freely in the other way. The rigid membrane 37 may be made permeable by means of a plurality of holes 41. The number, size and position of the holes may of course be varied according to the requested resistance to air. The flexible membrane 39 may be plain or may be provided with holes 43.

If the user of the device shown in FIG. 5 wants to stimulate his or her inspiratory muscles, the obstruction means 33 have to be positioned inside the air-duct 31 in such a manner that the flexible membrane bears against the solid membrane 37 to close the air duct and thus force the air inspired by the user through the holes 41 and the holes 43 if any. During expiration, air freely escapes through the conduit 32 by pushing out the flexible membrane 39, thereby making the air almost free to escape between the membranes 37 and 39. If the flexible membrane 39 is also provided with holes 43, these holes will of course decrease the resistance to the passage of air through the obstruction means 33.

If the user wants to exercise or stimulate his or her respiratory muscles, she or he only has to reverse the obstruction means 33.

Figure 2:
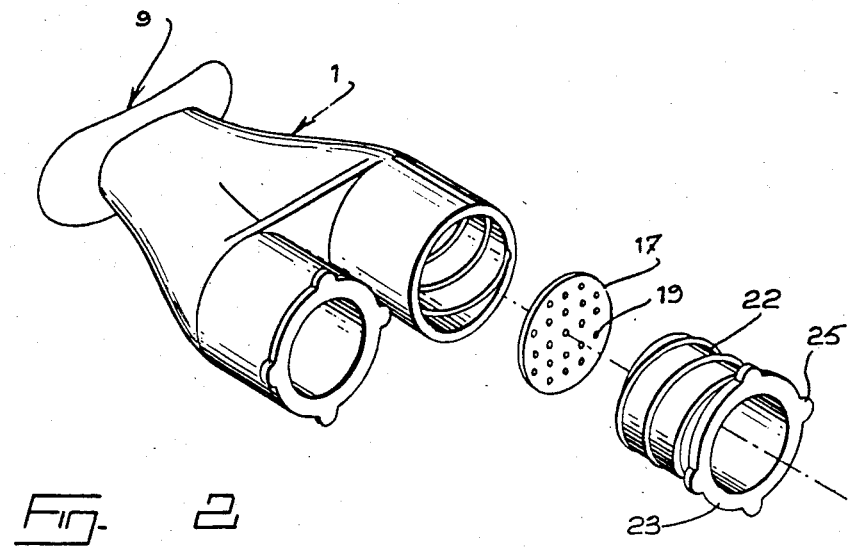
FIG. 2 is a partially exploded, perspective view of the device shown in FIG. 1, taken from a different angle.

Last of all, if the user wants to exercise both his or her inspiratory and expiratory muscles, the obstruction means 33 may be removed from the air duct 31 and replace by a perforated disc 17 like the one shown in FIGS. 2 and 3.

Figure 7:
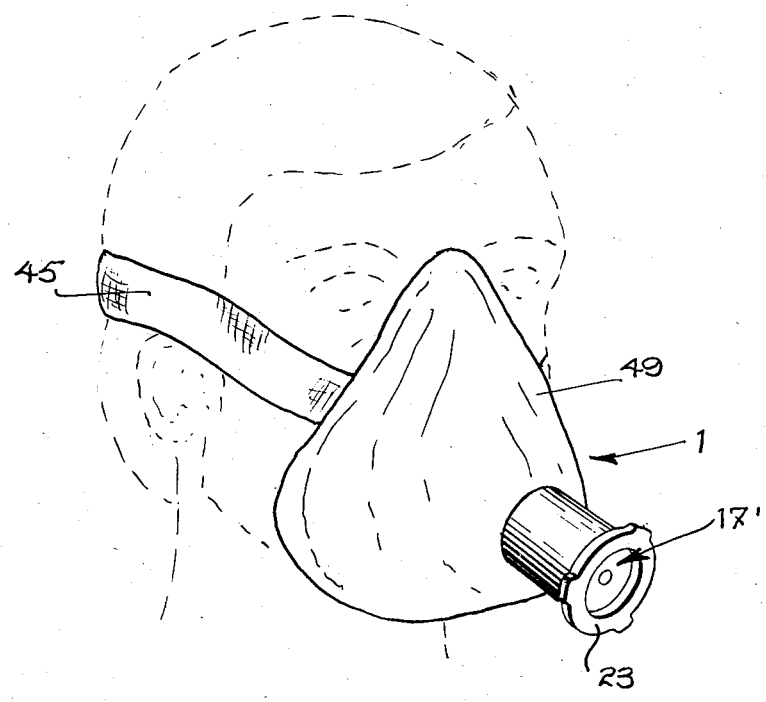
FIG. 7 is a perspective view of a further embodiment of the invention.

The device shown in FIG. 7 is of the same type as the one shown in FIG. 5, except that a mask 49 is used instead of a mouth-piece 9. This mask 49 which covers not only the mouth but also the nose of the user may be fixed to the user's face by means of a strap 45, in any conventional manner. The mask 49 is extended by an air duct 32 that can be similar to the one shown in FIG. 5 (as shown) or by a hollow body including a main air duct 3 and separate passages 5 and 7, like the one shown in FIGS. 1, 2 and 3.

The end of the air duct which opposite to the mask is provided with obstruction means that can be identical to the one shown in FIG. 6 when a hollow body such as the one of FIG. 5 is used, or similar to those described in connection with FIGS. 1 to 4 when a hollow body such as the one shown in FIGS. 1 to 3 is used.

Numerous modifications can be made to the three different embodiments described hereinabove, while remaining within the scope of the invention as defined in the appended claims.

Thus for example, it is not compulsory that the passages 5 and 7 (see FIG. 3) be parallel. As a matter of fact, these passages can be perpendicular or even aligned.

In FIG. 2 of the drawings, the ring 22 is screwed inside the passage 7. It can be easily understood that this ring may also be designed with a flexible peripherical bead having an external diameter sufficient to allow it to be locked inside the passage 7 when assembling the same.

A very important advantage of the device according to the invention is that the dead space provided by the passages and ducts 3, 5, 7 or 32 between the mouth-piece 9 or mask 43 and the obstruction means 17 and 33, substantially increases the dead respiratory volume of the user. As a result, a person practising with the device according to the invention is obliged to increase its lung ventilation without necessarily having to overcome the resistance of the membranes 17 and 33. This kind of constraint obliges the user to increase his inspiratory volume, and therefore the current volume of its lungs, instead of increasing his or her expiratory and inspiratory forces.

What is claimed is:

1. A device for simulating the human respiratory system by making breathing more difficult and limiting lung ventilation, said device comprising:
   a mouth-piece for insertion in the mouth of a person, said mouth-piece having a central opening through which the person may breathe,
   a tubular body defining an air duct, said tubular body being connected at one end to the mouth-piece with the air duct in alignment and communication with the opening of said mouth-piece, and
   obstruction means mounted in the tubular body at the other end thereof to put up a breathing resistance in both the inspiratory and expiratory directions, said mouth-piece, tubular body and obstruction means being very compact in size and light enough to be carried exclusively through the mouth-piece when the same is inserted in the mouth of the person, said tubular body further being long enough to increase the dead space of the respiratory system of the person using the device, wherein:

the air duct at the end of the tubular body opposite to the mouth-piece is divided into two parallel separate passages;

the obstruction means is mounted in only one of said passages and consists of a membrane permeable to air;

said obstruction means also comprises means to make it detachable and removable;

a check valve is mounted in the other passage to allow air to be freely breathed in at least one of the respiratory direction, said check valve comprising: means to make it detachable and reversible, thereby permitting selection of the direction in which air is allowed to be freely breathed in the passage in which said check valve is mounted.

2. A device for stimulating the human respiratory system by making breathing more difficult and limiting lung ventilation, said device comprising:

a mouth-piece for insertion in the mouth of a person, said mouth-piece having a central opening through which the person may breathe, a tubular body defining an air duct, said tubular body connected at one end to the mouth-piece with the air duct in alignment and communication with the opening of said mouth-piece, and obstruction means mounted in the tubular body at the other end thereof to put up a breathing resistance in both the inspiratory and expiratory directions, said mouth-piece, tubular body and obstruction means being very compact in size and light enough to be carried exclusively through the mouth-piece when the same is inserted in the mouth of the person, said tubular body further being long enough to increase the dead space of the respiratory system of the person using the wherein:

the air duct at the end of the tubular body opposite to the mouth-piece is divided into two parallel separate passages;

the obstruction means is mounted in only one of said passages and consists of an impermeable membrane provided with a central hole having a diameter smaller than the diameter of the passage in which said membrane is mounted said obstruction means also comprises means to make it detachable and removable;

a check valve is mounted in the other passage to allow air to be freely breathed in at least one of the respiratory direction, said check valve comprising: means to make it detachable and reversible, thereby permitting selection of the direction in which air is allowed to be freely breathed in the passage in which said check valve is mounted.

3. A device for stimulating the human respiratory system by making breathing more difficult and limiting lung ventilation said device comprising:

a mouth-piece for insertion in the mouth of a person, said mouth-piece for insertion in the mouth of a person, said mouth-piece having a central opening through which the person may breathe, a tubular body defining an air duct, said tubular body being connected at one end to the mouth-piece with the air duct in alignment and communication with the opening of said mouth-piece, and obstruction means mounted in the tubular body at the other end thereof to put up a breathing resistance in at least one respiratory direction, said mouth-piece, tubular body and obstruction means being very compact in size and light enough to be carried exclusively through the mouth-piece when the same is inserted in the mouth of the person, said tubular body further being long enough to increase the dead space of the respiratory system of the person using the device, wherein said obstruction means at the other end of the tubular body comprises:

a rigid membrane permeable to air, said membrane extending transversally across a portion of the air duct and providing a rigid edge transversal to said air duct; and a flexible membrane transversally mounted across the air duct, said flexible membrane covering the portion of said air duct not covered by the rigid membrane and overlapping at least part of the rigid membrane close to its rigid edge to form with said rigid membrane a check valve; whereby air is allowed to be freely breathed through this check valve in one respiratory direction while it is subject to breathing resistance through the rigid membrane in the other direction.

4. The device of claim 3, wherein the flexible membrane is also permeable to air.

5. The device of claim 4, wherein both membranes are fixed onto a same ring detachably mounted in a reversible manner in the tubular body.

* * * * *